United States Patent
Revinski et al.

(10) Patent No.: US 11,633,599 B2
(45) Date of Patent: Apr. 25, 2023

(54) DIGITALLY ADJUSTABLE PHRENIC NERVE STIMULATOR SYSTEM

(71) Applicants: NORTHWESTERN UNIVERSITY, Evanston, IL (US); ANN AND ROBERT H. LURIE CHILDREN'S HOSPITAL OF CHICAGO, Chicago, IL (US)

(72) Inventors: Alexey Revinski, Vernon Hills, IL (US); Kirby D. Gong, Verona, WI (US); Emma S. Cripe, Wheaton, IL (US); Michelle Wang, Naperville, IL (US); Matthew R. Glucksberg, Chicago, IL (US); Debra E. Weese-Mayer, Chicago, IL (US); Anthony Chin, Evanston, IL (US)

(73) Assignees: NORTHWESTERN UNIVERSITY, Evanston, IL (US); ANN AND ROBERT H. LURIE CHILDREN'S HOSPITAL OF CHICAGO, Chicago, IL (US)

( * ) Notice: Subject to any disclaimer, the term of this patent is extended or adjusted under 35 U.S.C. 154(b) by 35 days.

(21) Appl. No.: 16/652,737

(22) PCT Filed: Oct. 10, 2018

(86) PCT No.: PCT/US2018/055226
§ 371 (c)(1),
(2) Date: Apr. 1, 2020

(87) PCT Pub. No.: WO2019/075072
PCT Pub. Date: Apr. 18, 2019

(65) Prior Publication Data
US 2020/0238083 A1    Jul. 30, 2020

Related U.S. Application Data

(60) Provisional application No. 62/570,164, filed on Oct. 10, 2017.

(51) Int. Cl.
A61N 1/36    (2006.01)
A61N 1/378   (2006.01)
A61N 1/372   (2006.01)

(52) U.S. Cl.
CPC ........ *A61N 1/3611* (2013.01); *A61N 1/36034* (2017.08); *A61N 1/36125* (2013.01); *A61N 1/3787* (2013.01); *A61N 1/37235* (2013.01)

(58) Field of Classification Search
CPC .............. A61N 1/3611; A61N 1/36034; A61N 1/36125; A61N 1/37235; A61N 1/3787
(Continued)

(56) References Cited

U.S. PATENT DOCUMENTS 6,415,183 B1   7/2002  Scheiner et al.
7,970,475 B2   6/2011  Tehrani et al.
(Continued)

FOREIGN PATENT DOCUMENTS

WO    2005018737 A1    3/2005

OTHER PUBLICATIONS

Hofmann et al. "Modified pulse shapes for effective neural stimulation", Frontiers in Neuroengineering, vol. 4, 2011, URL=https://www.frontiersin.org/article/10.3389/fneng.2011.00009 (Year: 2011).*

(Continued)

*Primary Examiner* — Erin M Piateski
(74) *Attorney, Agent, or Firm* — Casimir Jones, S.C.; Brian F. Bradley (57) ABSTRACT

A system for electrical ventilation stimulation of a patient including an implantable nerve stimulator including a stimulation circuit and a pulse generator that produces biphasic charge-balanced pulses to stimulate a phrenic nerve, an external digital programming device having near field communication transmission and a digital interface, and wherein (Continued)

the external digital programming device is used to control settings of the implantable nerve stimulator.

7 Claims, 11 Drawing Sheets

(58) Field of Classification Search
USPC .......................................................... 607/42
See application file for complete search history.

(56) References Cited

U.S. PATENT DOCUMENTS

| | | | |
|---|---|---|---|
| 9,776,005 B2 | 10/2017 | Meyyappan et al. | |
| 2006/0122661 A1* | 6/2006 | Mandell | A61N 1/36139 607/42 |
| 2008/0287820 A1* | 11/2008 | Ignagni | A61B 5/389 600/529 |
| 2011/0190842 A1* | 8/2011 | Johnson | H01M 10/425 600/561 |
| 2012/0259389 A1* | 10/2012 | Starkebaum | A61B 5/686 607/62 |
| 2013/0090712 A1* | 4/2013 | Popovic | A61N 1/0476 607/148 |
| 2019/0022394 A1* | 1/2019 | Fayram | A61N 1/36062 |

OTHER PUBLICATIONS

Dimarco, Anthony F. et al., "Phrenic Nerve Pacing Via Intramuscular Diaphragm Electrodes in Tetraplegic Subjects", Chest, 127, Feb. 2, 2005, pp. 671-678.

Onders, Paymond P., "Characterization of the Human Diaphragm Muscle With Respect to the Phrenic Nerve Motor Points for Diaphragmatic Pacing", Mar. 2004.

United States Patent and Trademark Office (ISR/US), "International Search Report for PCT/US2018/055226", US, dated Jan. 10, 2019.

* cited by examiner

Figure 1a

| Acronym | Full Name | Min | Typ | Max |
|---|---|---|---|---|
| BR | Breathing Rate | 10bpm | 20bpm | 35bpm |
| IT | Inspiratory Time | 0.8s | 1.2s | 2.0s |
| PF | Pulse Frequency | | 20Hz | |
| PL | Pulse Length | 10us | 150us | 1000us |
| PM | Pulse Magnitude | 10uA | 2-5mA | 7mA |
| IPR | Inter-Pulse Resting Period | 100us | 3*PL | 1200us |
| SRS | Stimulation-to-Recharge Ratio | | 10 | |

| Phase | 1 | 2 | 3 | 4 |
|---|---|---|---|---|
| Phase Name | Stimulation | Inter-Pulse | Recharge | Resting |

| Component Model | Description | PCB Solution |
|---|---|---|
| STM8L152 C6T6 | 16MHz Low-power MCU with 12-bit DAC, 32KB FLASH, 2KB RAM, and 41 GPIOs | DAPhNe MCU |
| M24LR04 | 14x14mm double layer antenna reference board for the M24LR04E Dual Interface EEPROM | ANT7-T-M24LR04 |
| STWLC03 | Dual-mode Qi/ PMA wireless power receiver | STEVAL-ISB039V1 |
| MCP73831 | Miniature Single-Cell, Fully Integrated Li-Ion, Li-Polymer Charge Management Controller | (Breakout Board) |
| LTC3459 | 10V Micropower Synchronous Boost Converter | DAPhNe STIM |
| LT1492 | 5MHz, 3V/us, Low Power Single Supply, Dual Precision Op Amp | DAPhNe STIM |
| DMN1019U SN | 12v N-Channel Enhancement Mode MOSFET | DAPhNe STIM |
| TPS61200 | 0.3V Input Voltage Boost Converter with 1.3A Switches and 'Down Mode' in 3x3 QFN | Sparkfun PRT-10255 |
| ADG1636 | 1 Ω Typical On Resistance Dual SPDT Switch | (Breakout Board) |

| Phase | Stimulation (1) | Inter-Pulse (2) | Recharge Phase (3) | Rest Phase (4) |
|---|---|---|---|---|
| TIM1* Buffer | PL | IPR | PL*SRS | 1/BR-(PL+PL*SRS+IPR) |
| TIM2* Buffer | 0xFFFF | 50 clock cycles | 0xFFFF | 50 clock cycles |
| DAC Buffer | PM | PM/SRS | PM/SRS | PM |

* TIM1 and TIM2 are initialized to low polarity – Logic 0

| | |
|---|---|
| (1) | Pulse is of high magnitude, negative polarity, and 150 µs in length. Polarity is not switched within this period (pulse stays negative) |
| (2) | No pulse; polarity is almost instantly switched to positive, and magnitude is switched to "low" in preparation for upcoming re-charge pulse; duration: 450 µs |
| (3) | Pulse is of low magnitude and positive polarity; duration: 1500 µs. Polarity is not switched within this period (pulse stays positive) |
| (4) | No pulse; polarity is almost instantly switched to negative, and magnitude is switched to "high" in preparation for upcoming stimulation pulse; duration: the rest of the pulse period |

Figure 14

DIGITALLY ADJUSTABLE PHRENIC NERVE STIMULATOR SYSTEM

CROSS-REFERENCE TO RELATED APPLICATION

This application claims the benefit of U.S. Provisional Patent Application Ser. No. 62/570,164, filed Oct. 10, 2017, the disclosure of which is hereby incorporated by reference in its entirety.

FIELD OF THE INVENTION

The present disclosure generally relates to the field of controlling respiration of a patient, and more particularly to devices and methods used in providing stimulation pulses to the phrenic nerve to cause a diaphragm contraction and thereby provide a breath.

BACKGROUND OF THE INVENTION

Patients with conditions like Congenital Central Hypoventilation Syndrome (CCHS), quadriplegia and Amyotrophic Lateral Sclerosis (ALS) need continuous and prolonged artificial ventilation as life-support. External mechanical positive pressure ventilation and diaphragm pacing (a form of negative pressure ventilation) generally are regarded as the two most effective solutions.

Positive pressure ventilation may be provided by means of an external mechanical ventilator connected to the patient's airway via a tracheostomy. This has the clear disadvantages of requiring the tracheostomy and connection to cumbersome and heavy equipment that must always be with the patient.

During diaphragm pacing, the patient's diaphragm is either directly or indirectly stimulated with electrical pulses. Prior art devices that utilize direct diaphragm (muscle) stimulation require significant power usage. Phrenic nerve stimulation is an approach to diaphragm pacing that electrically stimulates the phrenic nerve (which intrinsically innervates the diaphragm), leading to diaphragmatic contraction and a breath. The current state-of-the-art phrenic nerve diaphragm stimulation system uses less power than a direct diaphragm stimulation system, but also relies on outdated analog technology. Such technology requires the patient to be tethered to an external control device (a transmitter) throughout pacing, and offers limited programming options that must be modified with a small handheld phillips screwdriver.

A more physiologically-appropriate approach is provided by the currently available Avery Breathing Pacemaker, a diaphragm pacing system manufactured by Avery Biomedical Devices, which is the only FDA-approved phrenic nerve stimulator system known to the inventors. It is a system that accomplishes some physiological needs and consists of an external analog radio-frequency (RF) transmitter and bilaterally subcutaneously implanted short-range RF receivers. The patient is required to be tethered to two antenna coils attached to the external transmitter. The transmitter generates RF signals and transfers them using external the antennae attached to the patient's body directly over the subcutaneous bilaterally-implanted receivers.

The receivers' analog circuit transduces the signal into simulation pulses, which travel along the stainless steel wires to the specially designed phrenic nerve electrodes placed thoracoscopically in the chest (bilateral electrodes and connecting wires linking to the subcutaneously implanted receivers). The pulses pass from the electrodes to the respective phrenic nerves, the nerves stimulate the diaphragm, and a breath is generated. However, the Avery system has notable disadvantageous limitations. The system offers only one respiration mode per transmitter (such as walking, running or sitting), has limited versatility with respect to use during serious exercise (does not provide adequate ventilator support to avert low oxygen and increased carbon dioxide), requires external batteries (fit into the external transmitter) and cumbersome wearable external components (the transmitter and the two antennae). The external transmitter takes on all of the control functionality, so without it (via the antennae) actively transmitting in immediate range of the subcutaneously implanted receivers, stimulation and artificial breathing are not possible. The external transmitter also offers less than reliable metrics for adjusting its respiration settings and the physician and technical team have to manually adjust the system by hand (using a miniature phillips screwdriver and a flashlight), viewing the output using surface Electromyography (EMG) electrodes that are pre-amplified then seen on a digital oscilloscope.

SUMMARY

This disclosure presents a new digitally adjustable phrenic nerve (DAPhNe) stimulator system that is directed to patients who acquire, genetically or otherwise, severe autonomic nervous system disorders that result in prolonged hypoventilation, often with abnormal responses to low oxygen or elevated carbon dioxide. The new system addresses and overcomes limitations in the prior art.

In a first aspect, the disclosure provides a system for electrical ventilation stimulation of a patient that includes an implantable nerve stimulator including a stimulation circuit and a pulse generator that produces biphasic charge-balanced pulses to stimulate a phrenic nerve, an external digital programming device having near field communication transmission and a digital interface, wherein the external digital programming device is used to control settings of the implantable nerve stimulator.

In a second aspect, the disclosure provides a method of using an implantable nerve stimulator for electrical stimulation to control ventilation of a patient that includes surgical placement of an implantable nerve stimulator in the patient that produces charge-balanced pulses to stimulate a phrenic nerve, and utilizing an external digital programming device to program settings of the implantable nerve stimulator with respect to parameters and modes for wireless operation of the implantable nerve stimulator.

The digitally-adjustable phrenic nerve stimulator system includes an implantable stimulator and an external controller that wirelessly communicates with the stimulator. The part of the system that is implantable electrically stimulates the patient's phrenic nerves, which innervate the diaphragm muscle and provide a natural way for the patients to breathe. Thus, this approach avoids prior art external mechanical positive pressure ventilation and direct stimulation of the diaphragm muscle in pacing. While the system originally was designed to target CCHS, it is applicable to any other hypoventilation-inducing conditions, in which a long-term solution is necessary or desired.

As above noted and explained further herein, the example digitally-adjustable phrenic nerve (DAPhNe) stimulator system and example methods of using the same of this disclosure provide several advantageous features. It also is to be understood that both the foregoing general description and the following detailed description are exemplary and provided for purposes of explanation only, and are not restrictive of the claimed subject matter. Further features and objects of the present disclosure will become more fully apparent in the following description of the preferred embodiments and from the appended claims.

BRIEF DESCRIPTION OF THE DRAWINGS

In describing the preferred embodiments, reference is made to the accompanying figures wherein like parts have like reference numerals, and wherein:

FIG. 2a-2d provide stimulation electrode voltage potential with respect to body ground, normalized by tissue impedance: with the time scale in FIG. 2a being seconds over multiple breaths and showing inspiratory and expiratory phases; the time scale in FIG. 2b being tens of milliseconds and showing two pulse cycles; the time scale in FIG. 2c being hundreds of microseconds and showing a single pulse cycle.

It should be understood that the drawings are not to scale. While some details of the example digitally-adjustable phrenic nerve stimulator system, including potential alternative configurations, have not been included, such details are considered within the comprehension of those of skill in the art in light of the present disclosure. It also should be understood that the present invention is not limited to the example embodiments illustrated.

DETAILED DESCRIPTION OF THE PREFERRED EMBODIMENT

Figure 1A:
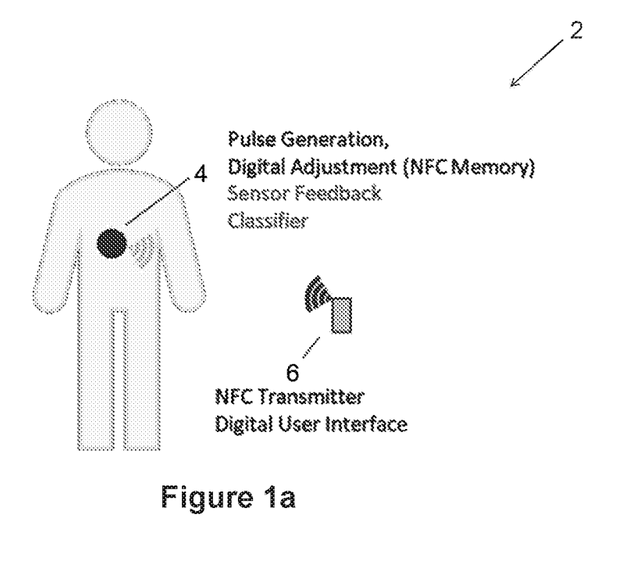
FIG. 1a shows a system having an implanted stimulator and external controller.

A digitally adjustable phrenic nerve stimulator system 2, shown in FIG. 1a, is provided as a direct improvement over the prior art systems. The system includes an implanted stimulator or digital implant 4 and an external controller 6. The implant 4 provides pulse generation, with digital adjustment via wireless Near Field Communications (NFC) technology. The external controller 6 includes an NFC transmitter that provides a digital user interface.

Overview of Stimulator Implant and External Controller

As opposed to prior art mechanical ventilation, the system 2 uses the body's own phrenic nerve-diaphragm connection to induce diaphragm contraction, thereby making a breath. Thus, by providing stimulation pulses to the nerve, the implanted stimulator 4 causes the diaphragm to contract. This develops negative pressure on inspiration (with respect to atmospheric) inside the patient's airways, drawing oxygenated air into the lungs. Upon rest, the diaphragm relaxes and exhalation occurs.

The digitally adjustable system 2 accomplishes diaphragm pacing by using stimulation pulses that reach the nerve through an embedded electrode, but the digital implant 4 is able to autonomously generate its own simulation pulses without the need for an external controller that must be in constant communication or for the patient to wear cumbersome external components. The digital implant 4 includes a stimulation circuit and generates biphasic charge-balanced pulses to stimulate the phrenic nerve. Use of monopolar nerve stimulation while balancing electrical charge passing through the tissue helps to prevent nerve damage due to long term stimulation. The system 2 is very efficient with respect to power consumption, because it only stimulates two nerves. This allows the implant 4 to be battery powered and responsible for stimulation output generation and proper breathing control on its own.

The system's external controller 6 is used to wirelessly program new breathing mode parameters into the implant's software. The external controller 4 is used to change the pulse settings of the implant 4, permitting multiple programmable breathing parameters and modes. The controller 6 and implant 4 communicate via wireless NFC technology and the lithium ion battery in the implant 4 may be wirelessly charged. Wireless control allows the patient to remain untethered to any external devices. It is further contemplated that use of bio-feedback mechanisms may allow the system to become almost completely autonomous, eliminating the need for regular control with an external device.

The digitally adjustable phrenic nerve stimulator system 2 enhances mobility of patients in need of continuous artificial ventilation and supports a wider range of exertional activities, compared to prior art systems. The new system 2 provides patients and healthcare personnel with an intuitive, wireless, multi-modal system that supports a range of breathing modes to provide artificial ventilation for life-support in age-appropriate activities of daily living. The system includes a digital wireless handheld external controller 6 and a battery-powered implantable stimulator 4. The implant 4 is capable of autonomously stimulating the phrenic nerve, while the external controller 6 is used by a physician or healthcare personnel to program various breathing parameters and modes unique to each patient, which may permit patients to switch between preprogrammed breathing modes. Thus, upon changing breathing modes (i.e. from "walking" to "running" or "sitting", "eating", etc.), the external device 6 communicates new breathing parameters to the implant 4 via NFC technology. The implant 4 autonomously provides breathing control at the desired settings, while the external controller 6 is only used to switch the implant 4 from one mode to another on a per breath basis.

The implantable stimulator 4 performs phrenic nerve stimulation for long-term ventilatory support with multi-modal capabilities and breath-to-breath control. The implant 4 includes a microcontroller and a stimulation circuit. The device draws current through the tissue by means of a hemi-cuff electrode and a subcutaneous anode plate. This new system 2 supports a wider range of patient activities and allows for increased patient mobility compared to prior art systems. The easily adjustable digital nature of the system will improve control over breathing modes by patients and healthcare professionals.

Constant-Current Stimulation

To stimulate the neural tissue, the system 2 applies a constant current through the phrenic nerve. This is referred to as constant-current stimulation (CCS). CCS pulls a constant current through the load no matter the tissue impedance, which ensures proper neural excitation at each stimulation pulse. CCS leads to relatively larger power consumption than use of a constant-voltage stimulation (CVS) system, but provides more reliable stimulation. Because the focus of the system 2 is on patient treatment, support, and reliability, the implanted stimulator 4 employs CCS to achieve phrenic nerve excitation. Hence, it pulls a programmable current through tissue, limited only by the device's rail-to-rail power supply.

Charge Balancing Biphasic Stimulation

As the charge is injected into the tissue, it disrupts the electrical potential balance in neural cells. The body naturally achieves ionic balance in the tissue via cellular pumps and channels, but this process happens gradually. Stimulation devices usually do not balance the charge they inject into the tissue. While this is a tolerable short-term solution, prolonged unbalanced solutions may not be suitable for patients.

To combat this issue, some researchers have used a biphasic stimulation pattern using dual power supplies. In effect, a negative stimulation pulse depolarizes the nerve, and the following positive re-charge pulse balances out the injected charge. The present system 2 provides a solution to this as well. It generates a positive re-charge pulse that has a much smaller magnitude but takes place for a longer time period than the negative stimulation pulse. By matching the total amount of charge exchanged during each positive and negative pulse, the implanted stimulator 4 takes care of the charge-balancing problem, but also prevents the unwanted anodic stimulation.

Device Output

Based on the above considerations, the output of the system 2 consists of biphasic pulses and the stimulation electrode voltage potential with respect to body ground, normalized by tissue impedance is depicted in FIGS. 2a-2d.

Programmable Parameters

Figure 1B:
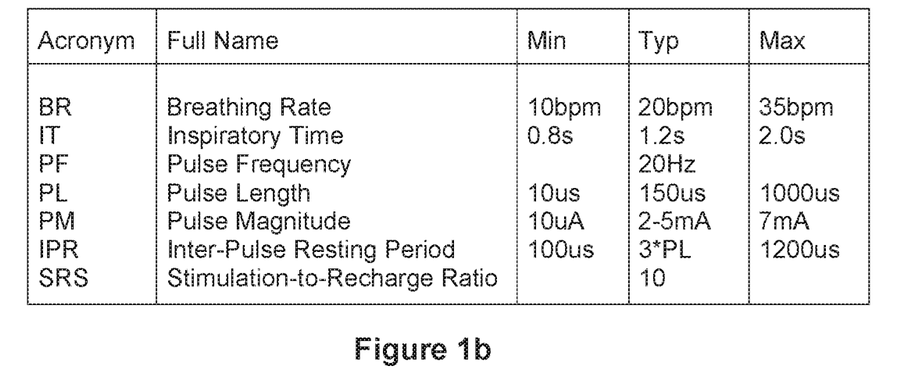
FIG. 1b is a table listing device output parameters in the form of breathing parameter settings.

The system has full control of all the depicted parameters, and FIG. 1b provides a table of the breathing parameter settings satisfied by a prototype of the implant 4. With respect to the parameters, it should be understood that most minimum and maximum values would be limited in software to ensure patient safety and further evaluation will be required to determine absolute minimum and maximum values that should be allowed by the device.

Output Waveform

Figure 2A:
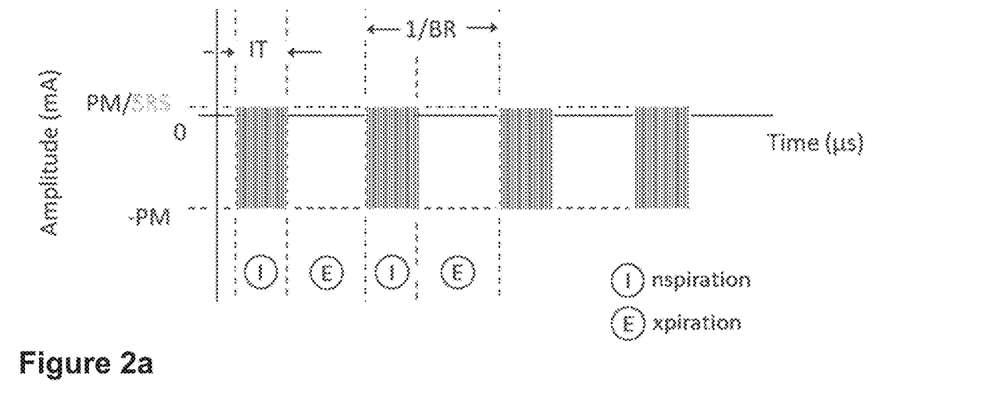
Figure 2B:
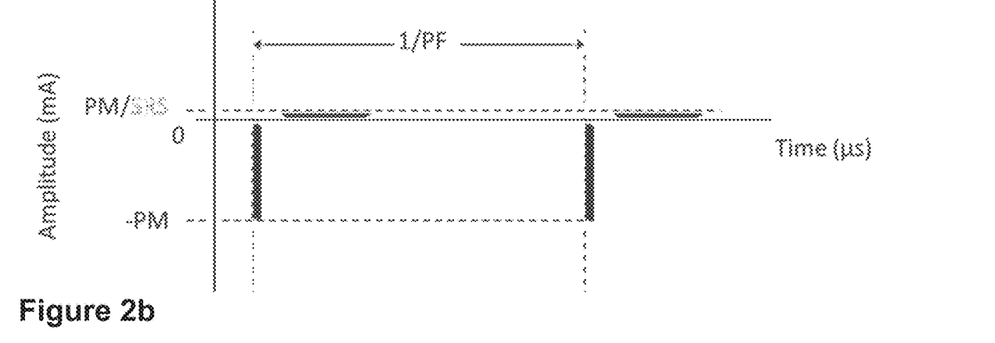
Figure 2C:
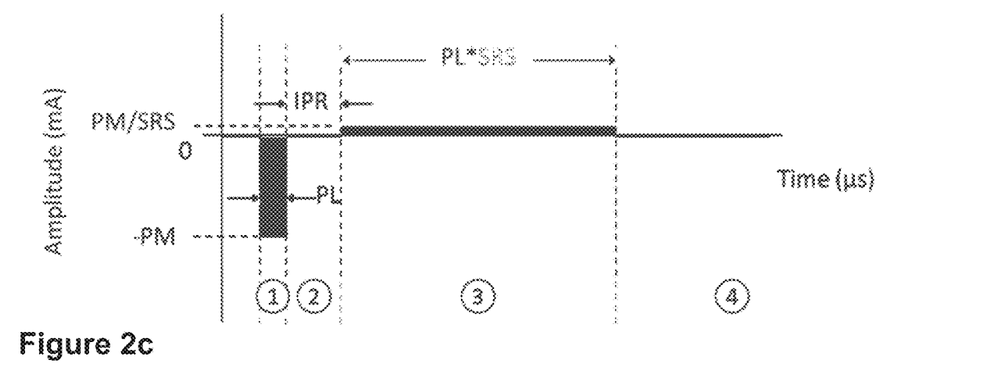
Figure 2D:
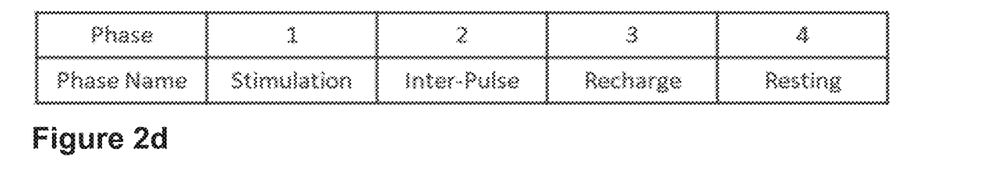
FIG. 2d showing pulse phases referenced through this disclosure.

Turning to FIGS. 2a-2d, one can appreciate that FIG. 2a has a time scale in seconds for multiple breaths, showing inspiratory and expiratory phases, and that on the breath-to-breath scale shown in FIG. 2a, the system 2 has full control of the patient's breathing rate and inspiratory time. FIG. 2b has a time scale in tens of milliseconds and shows two pulse cycles. For optimal physiological stimulation, the pulse cycles are generated at 20 Hz, with the higher frequencies allowed to smooth out the contraction curve seen in FIG. 2b. FIG. 2c has a time scale in hundreds of microseconds and shows a single pulse cycle. The pulses themselves are generated having four phases, as shown in FIG. 2c. FIG. 2d refers to the pulse phases referenced throughout the document. The actual stimulation pulse is followed by a period of rest (IPR), followed by a recharge pulse smaller than the stimulation pulse in magnitude and larger in length by a certain Stimulation-to-Recharge Scaling (SRS) ratio. For example, with SRS=10, the recharge pulse is 10 times longer than the stimulation pulse, but also 10 times smaller in magnitude. This allows for the positive pulse to assume a low magnitude, yet completely balance the charge injected into tissue. The fourth phase is the resting phase, during which no signals are generated until the next pulse cycle.

Stimulation Control Signal

Figure 3A:
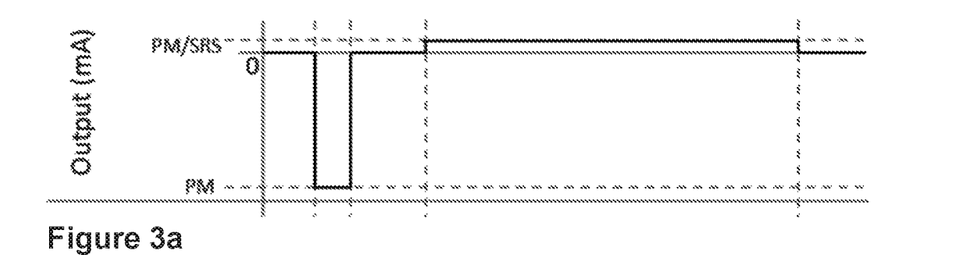
FIGS. 3a-3d show how three control signals control device output, with FIG. 3a showing a desired device output signal, FIG. 3b showing pulse timing logic input, FIG. 3c showing pulse polarity logic input, and FIG. 3d showing pulse magnitude control input.
Figure 3B:
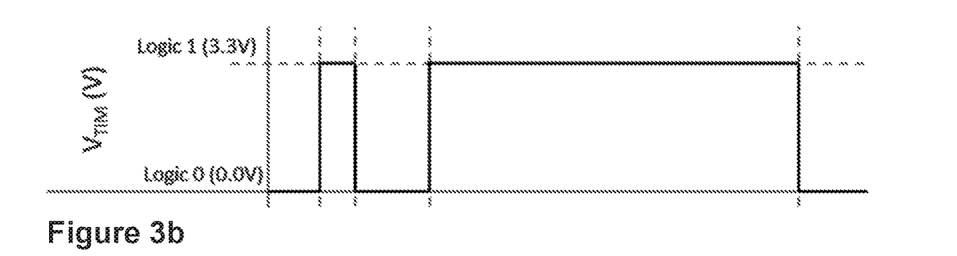
Figure 3C:
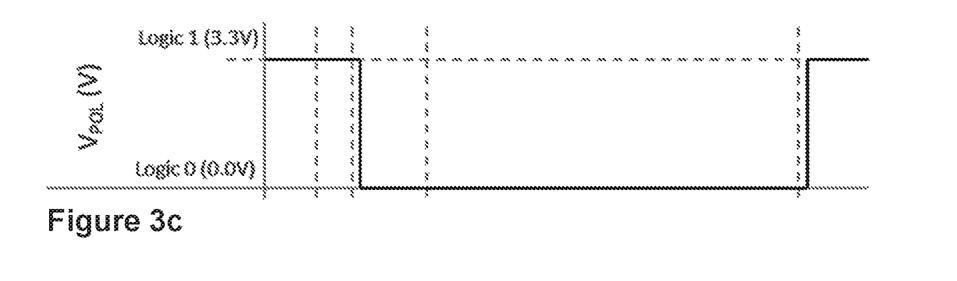
Figure 3D:
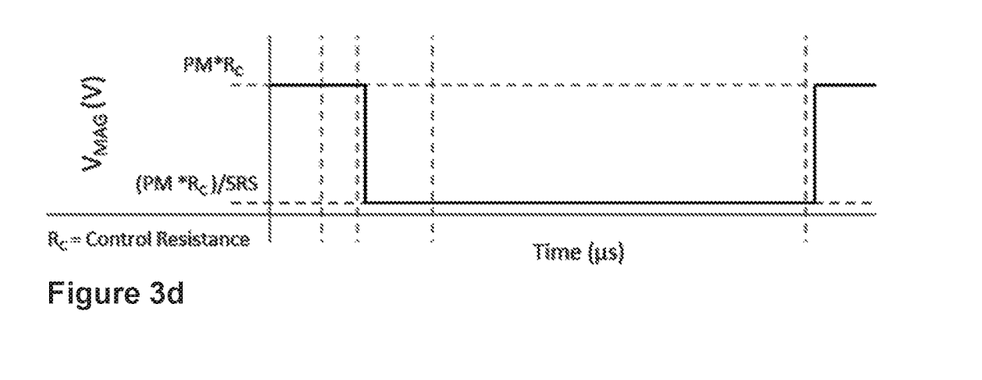

To achieve the device output shown in FIGS. 2a-2d, the implanted stimulator includes an embedded microcontroller. The microcontroller provides the following three control signals to a hardware stimulation circuit: pulse timing logic (on/off), referred to hereinafter as VTIM; pulse polarity logic (positive/negative), referred to hereinafter as VPOL; and pulse magnitude analog signal, referred to hereinafter as VMAG. FIGS. 3a-3d show how the three signals control device output during all four phases of the pulse cycle. FIG. 3a shows an example desired device output signal; FIG. 3b shows an example pulse timing logic input signal; FIG. 3c shows pulse polarity logic input; and FIG. 3d shows an example pulse magnitude control input signal.

Example Hardware Prototype

Figure 4:
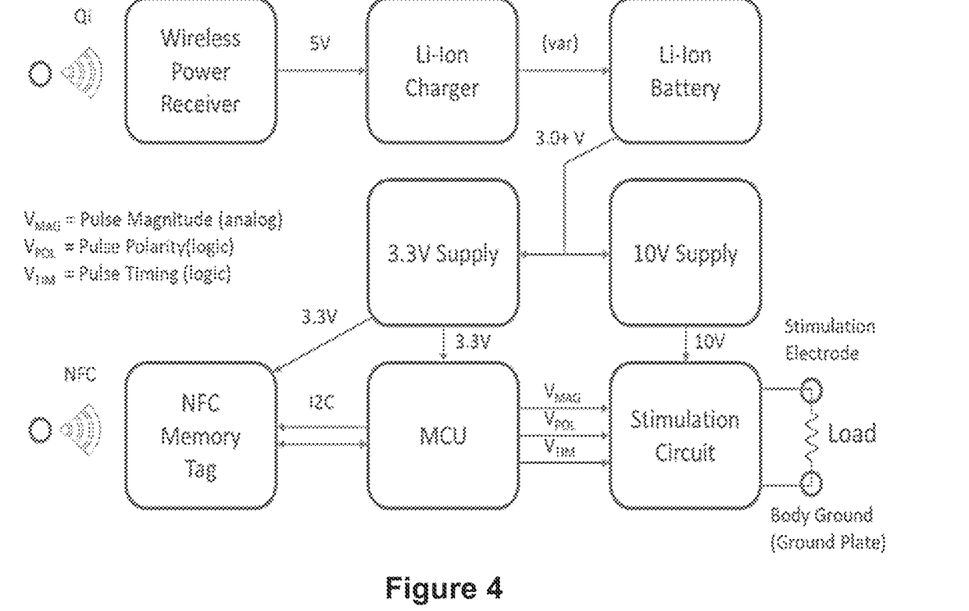
FIG. 4 shows an overall hardware diagram for the stimulation implant.

FIG. 4 shows a hardware module diagram for a prototype. The device is powered by a 3.7V Lithium Ion battery, which is charged wirelessly using a Qi-capable power receiver SoC through the patient's thin skin layer. The battery supplies energy to two voltage supplies. The 3.3V supply powers the embedded microcontroller (MCU) and the wireless NFC memory; the 10V boost supply powers the stimulation circuit. The device draws current through the tissue by means of a hemi-cuff electrode and a subcutaneous anode plate.

Stimulation Circuit

Figure 5:
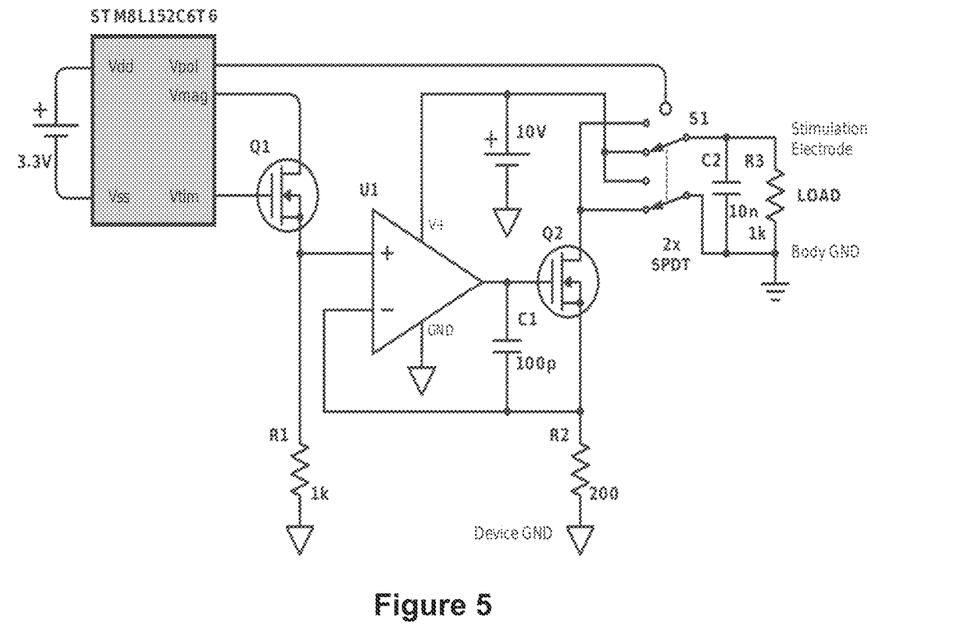
FIG. 5 shows a theoretical stimulation circuit.

With respect to previously mentioned FIGS. 3a-3d, the microcontroller outputs three control signals that interface with a stimulation circuit of the stimulation implant 4. The theoretical stimulation circuit, along with a "summarized" depiction of the microcontroller is shown in FIG. 5. The circuit consists of a programmable current sink, a polarity switching circuit, and a "valve" MOSFET switch (Q1) controlling the current sink, Current Sink Circuit The programmable current sink is implemented with a precision op-amp, a low Rdson MOSFET, and a high-precision current flow control resistor (R2). The voltage potential applied to the positive terminal of the op-amp appears at the R2-Q2 node in the circuit via negative feedback; this establishes a certain current over R2. With a value of 200Ω, 1V at the positive terminal of the op-amp results in 5 mA of current flowing through R2. The op-amp outputs just enough voltage to the gate of Q2 as to establish this current through R2 and equate the potential at its positive and negative terminals.

Current flowing through R2 comes only from the source of Q2. Assuming the dual SPDT switch is configured in such a way that the load is in series with Q2, all of this current also flows through the load. In this way, a programmable current is pulled through the load, no matter its actual impedance.

Control Switch

The Q1 MOSFET acts as a "valve" for the VMAG signal output from the microcontroller; the gate of Q1 is connected to VTIM output. So, when VTIM is high, Q1 fully conducts (VTIM is always greater than VMAG, which is in the range of 0-2V), and VMAG appears at the positive terminal of the op-amp, forcing current to flow through the load. When VTIM is low, Q1 does not conduct; the positive terminal of the op-amp is pulled to device ground by R1, and no current flows through the load.

Polarity Switching Circuit

Figure 6:
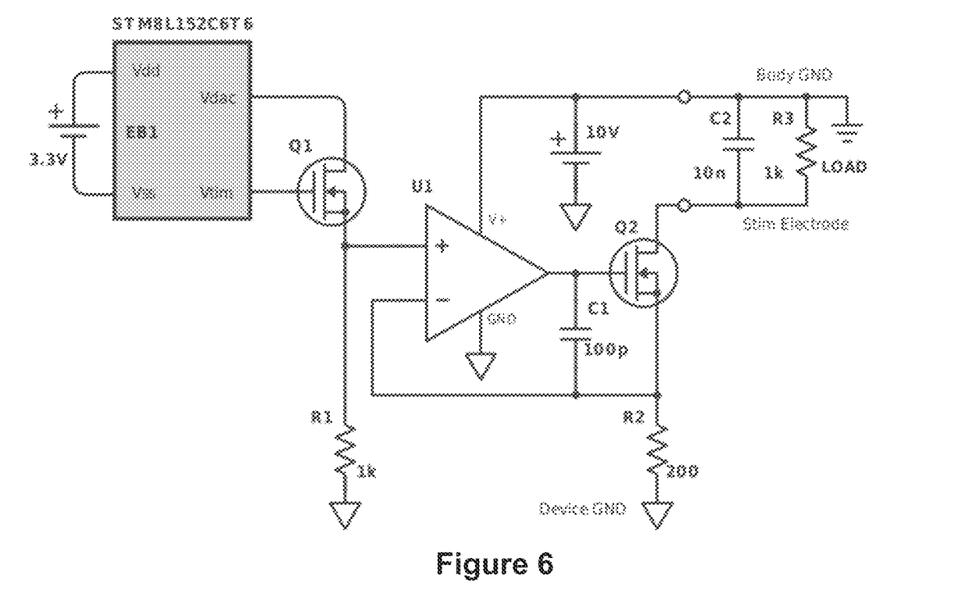
FIG. 6 shows an equivalent circuit when pulse polarity control signal (VPOL) is high.

The signal VPOL controls the orientation of the dual SPDT switch. Both SPDT branches of the switch are tied together to VPOL—they are both switched when VPOL changes. When VPOL is high, the equivalent circuit is shown in FIG. 6. Body ground is connected to the 10V source, and stimulation electrode—to the drain of Q2. When Q2 conducts, current flows from body ground to the stimulation electrode—electrode is driven low with respect to body ground.

Figure 7:
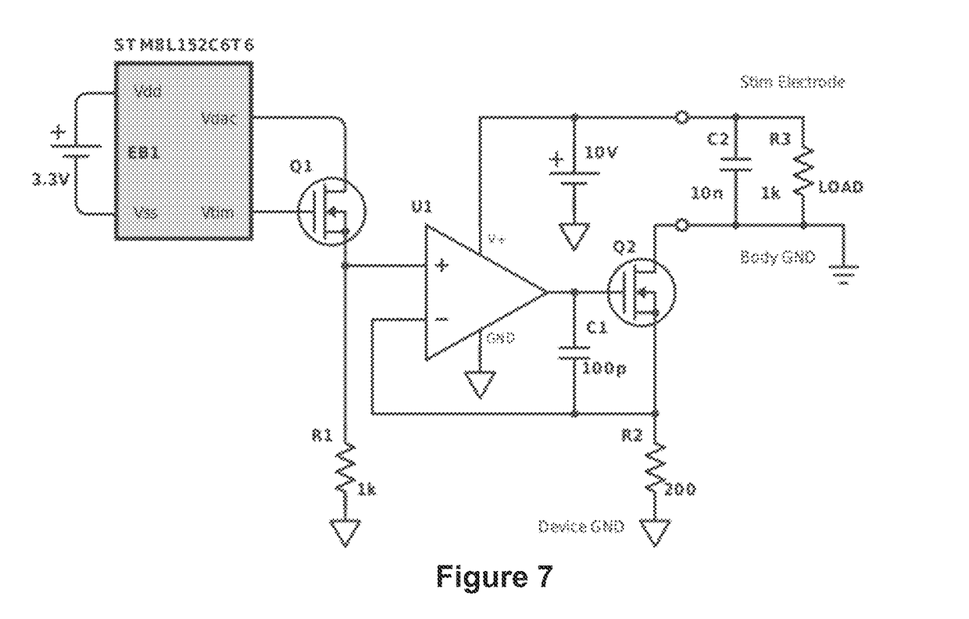
FIG. 7 shows an equivalent circuit when pulse polarity control signal VPOL is low.

Alternatively, when VPOL is driven low, the equivalent circuit is shown in FIG. 7. In this case, the stimulation electrode is connected to the 10V source, and body ground—to the drain of Q2. When Q2 conducts, the electrode is driven higher than body ground, and current flows in the opposite direction, balancing the charge pulled through tissue during a previous negative pulse. Capacitor C1 prevents spikes appearing at the output of the op-amp as a result of sudden switching of Q1, and C2 smooths out the spikes caused by sudden switching of Q2. Both capacitors are there to smooth out current spikes through the tissue.

Device Circuit Diagram

Figure 8A:
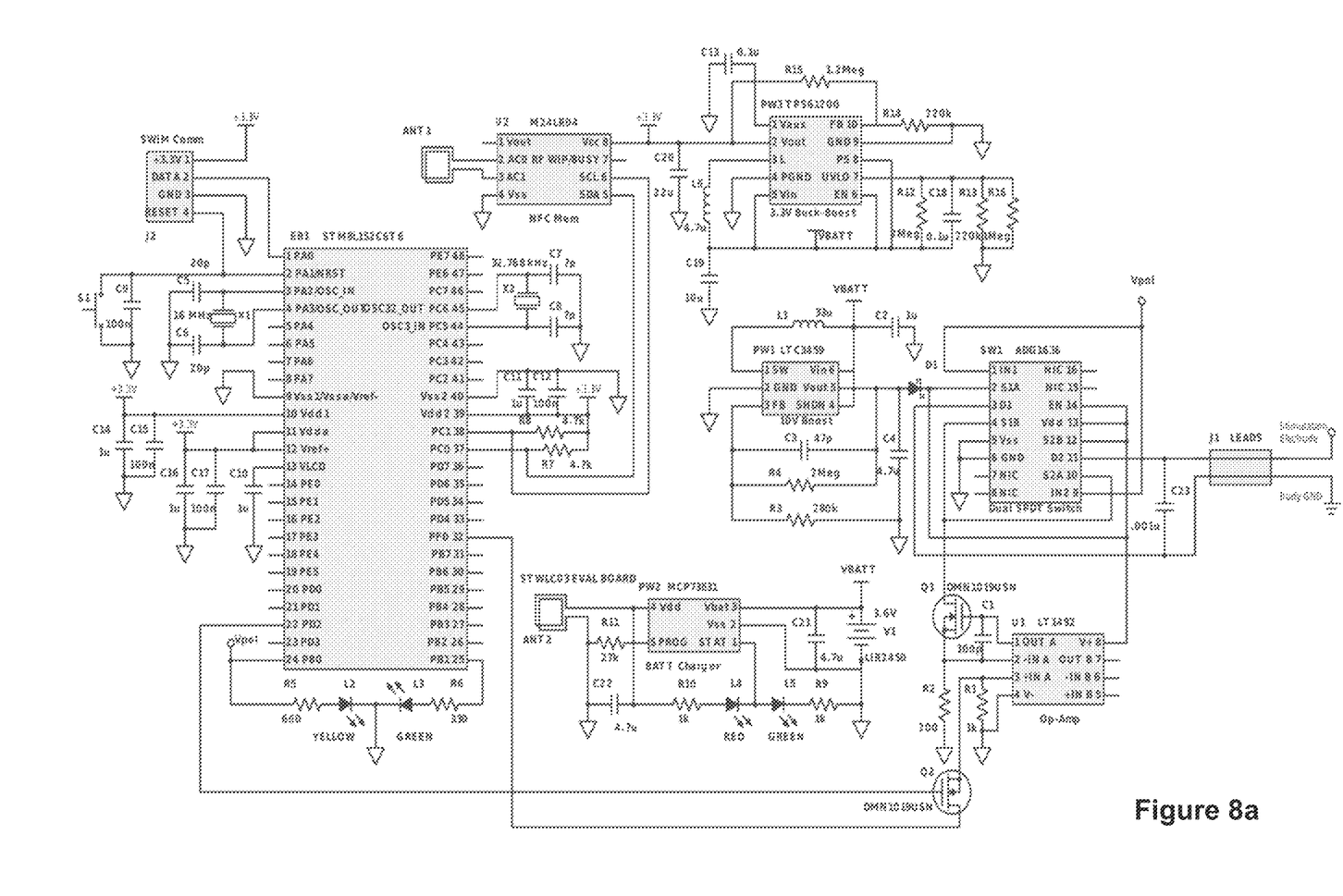
FIG. 8a shows a circuit diagram of the digitally-adjustable phrenic nerve (DAPhNe) stimulator prototype.
Figure 8B:
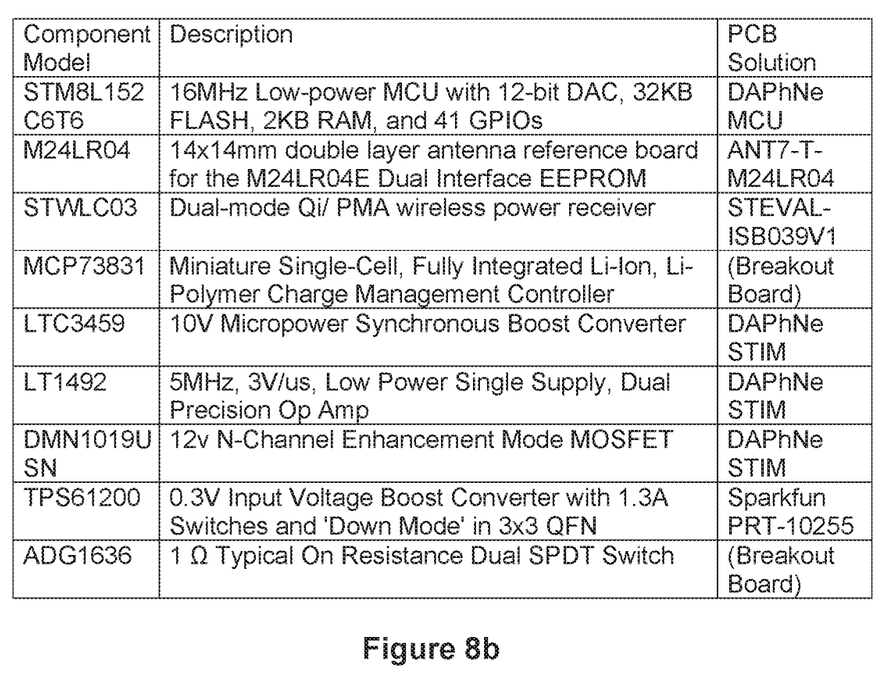
FIG. 8b is a table listing active and passive components used in the DAPhNe stimulator prototype.

FIG. 8a shows the overall device circuit diagram. No device protection features have been incorporated into the design yet—only functionally relevant components described below. FIG. 8b provides a table listing the active and special passive components used in the prototype.

Prototype Hardware Design

Figure 9:
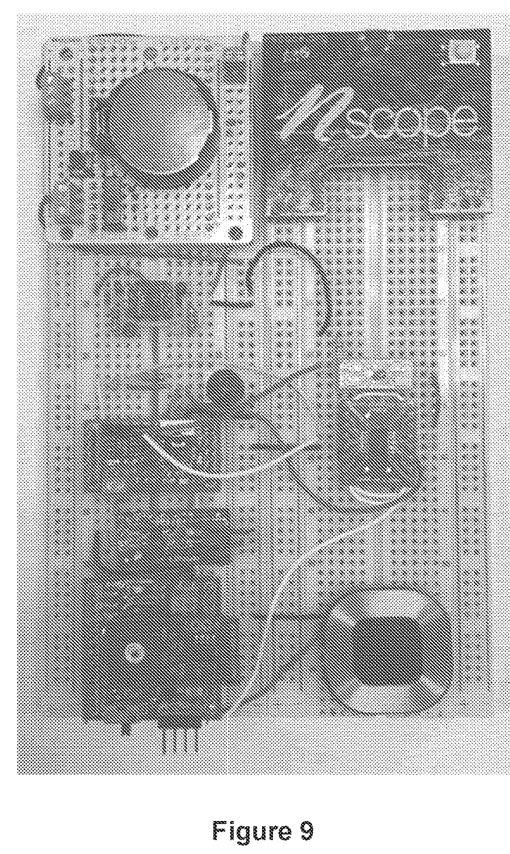
FIG. 9 is an enlarged photograph of the prototype DAPhNe stimulator.

The current prototype incorporates some of the above components in custom-designed PCBs, and others as part of third-party solutions, some of which are open-source devices. An enlarged photograph of the current prototype stimulator is shown in FIG. 9. FIG. 8a lists the active and special passive components used in the prototype.

Battery

The battery powering the current prototype is LIR2450H, a 190 mAh rechargeable Li-Ion coin cell. A breakout board was designed for this battery size (large square white-colored prototyping board on top left of FIG. 9). It features a 2450-size battery holder, a push button (SPST) and an SPAT switch, with multiple screw-in ports for the positive and negative terminals of the battery.

3.3V DC Supply

The prototype is powered by the aforementioned Li-Ion battery. Batteries of this type can assume close to 4.0 V when fully charged, and go down to 3.0V when discharged. Yet, the chosen microcontroller is most stable at a 3.3V supply. So, a simple buck converter or a linear regulator cannot be used, as the battery voltage can dip below 3.3V for some portion of the discharge cycle. A buck-boost converter, however, is very suitable.

The stimulator prototype uses a 3.3V DC supply board by SparkFun, LiPower PRT-10255. It powers the microcontroller, NFC memory chip, and related circuitry. At the heart of the board is the TPS61200 buck/boost converter from Texas Instruments, which features programmable voltage output, over temperature protection, and an undervoltage lockout (UVLO) feature.

The latter feature makes sure the battery is not overdrawn by the rest of the circuit. At a certain programmable low voltage threshold, the converter essentially disconnects the battery supply from the rest of the circuit. On the LiPower board, this threshold was adjusted to about 3.0V by soldering a 1 MΩ resistor (R16) in parallel with R13 (see the circuit diagram in FIG. 8a). While this power supply board from SparkFun is a good short-term solution, it will be appreciated that a microcontroller running on a sub-2V supply may be used and, in that case, a simple buck-converter with a UVLO-like feature may be used.

Charging Circuitry

The battery of the device is wirelessly charged using a Qi-compatible device. In the current prototype, the wireless power receiver is an evaluation board from ST Microelectronics that uses their STWLC03 Dual Mode Qi/PMA power receiver IC, STEVAL-ISB039V1R. The external transmitter that supplies energy to the STWLC03 board is the STEVAL-ISB039V1T board, based on ST's 32-bit ARM-Cortex M0 STM32F0 microcontroller.

The STEVAL-ISB039V1R board supplies a constant 5V when the transmitting board's wireless coil is in range of reception. This 5V supply is then used by a Li-Ion charge management controller from Microchip Technology, MCP73831, to charge the LIR2450H battery. MCP73831 is a complete charging solution for Li-Ion batteries, and features multiple charging modes (Preconditioning, Fast Charge, Constant Voltage—all internally managed), and a UVLO feature like TPS61200. The charging cycle only starts once the supply voltage from STWLC03 rises above about 3.4V. The MCP73831 chip also features a tri-state status pin; LEDs L4 and L5 in the circuit diagram in FIG. 8a are used in this prototype to visually monitor the status of the battery when charging.

NFC Memory Antenna Board

Figure 11:
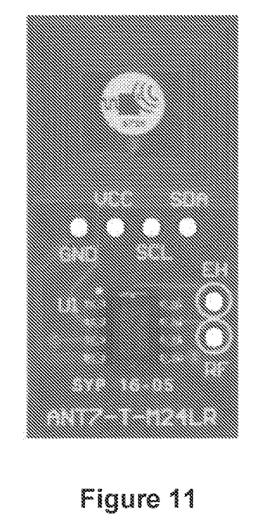
FIG. 11 is an enlarged photograph of an ANT7-T-M24LR04 Near Field Communication (NFC) Antenna Board.

As a great substitute for a custom NFC antenna interface, the ANT7-T-M24LR04 reference board from STMicroelectronics shown in FIG. 11 is used as a passive NFC receiver tag in the current prototype. It features a 14 mm×14 mm NFC antenna, and DIP-style holes for breakout pins for its power supply and I2C interface data pins.

Breakout Board Components

MCP73831 (Li-Ion charging IC), ADG1636 (SPDT switch IC), and a Schottky diode used to prevent current backflow into the 10V supply (when it is off) from digital inputs of ADG1636 were installed in the prototype using breakout boards.

DAPhNe MCU v 1.0 Printed Circuit Board

Figure 10:
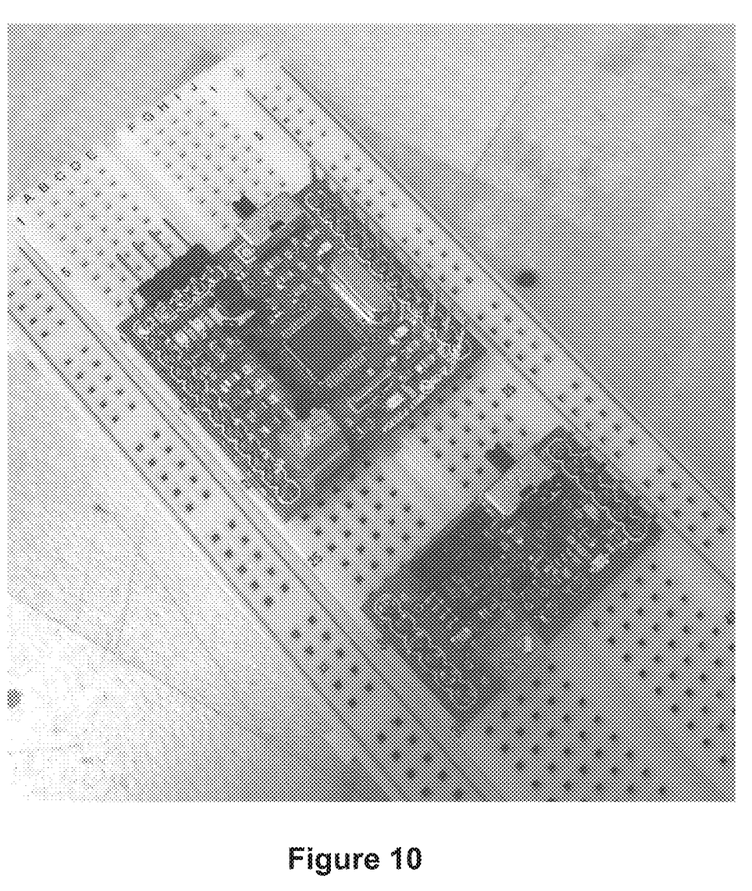
FIG. 10 is an enlarged photograph of custom printed circuit boards (PCBs) for the DAPhNe microcontroller unit (MCU) (top left in photograph) and the DAPhNe stimulation circuit (STIM) (bottom right in the photograph)

A custom PCB design has been developed for the microcontroller that houses the device's software (see FIG. 10, top left). The board also acts as a plug-in receiver for the ANT7-T-M24LR04 board (see FIG. 9, bottom left). The DAPhNe MCU is a two-layer PCB that features:

STM8L152C6T6 microcontroller.

16 MHz external crystal oscillator used to clock CPU and other peripherals.

32.768 kHz external crystal oscillator used for the Real Time Clock (RTC) peripheral.

0805 package passives.

On/off switch, connecting the 3.3V supply from TPS61200 to the rest of the board.

Power status LED.

Two general-use LEDs for firmware debugging.

Screw-in port for the power supply wires.

Four-0.1'-male-header-pin interface to the ST-LINK/V2 debugger tool.

24 0.1" DIP-style breakout pins, used partly to securely position the PCB on a breadboard and partly as signal output pins, to be interfaced with DAPhNe STIM and other boards in the prototype.

Four-0.1"-pin female connector that acts as a plug port for the ANT7-T-M24LR04 NFC board.

Push-button used to reset the MCU.

After the DAPhNe MCU v1.0 was designed and incorporated into the prototype, one of the MCU pins that was merely used to drive a blue LED for debugging (PB0) actually got an essential role in the device functionality (pulse polarity control signal), and had to be connected to one of the free breakout pins on the PCB by an external wire.

DAPhNe STIM v 1.0 Printed Circuit Board

A custom PCB design was developed for the stimulation circuit (STIM), excluding the polarity switch IC (see FIG. 10, bottom right, and FIG. 9, middle left). The polarity-switching circuit is housed externally using standard break-out boards (FIG. 9, middle right). The DAPhNe STIM PCB was originally designed to plug in directly into the DAPhNe MCU board, but was installed separately in the prototype. DAPhNe STIM is a two-layer PCB that features:

LTC3459 10V boost-converter.

LT1492 single supply dual precision op-amp.

DMN1019USN 12V N-channel enhancement mode MOSFETS.

0805 package passives.

On/off switch that connects the battery power supply to the rest of the board.

Power status LED.

Twelve 0.1" DIP-style breakout pins, used partly to securely position the PCB on a breadboard and partly as signal input/output pins, to be interfaced with DAPhNe MCU and other boards in the prototype.

Four-0.1"-pin female connector that acts as a breakout connector for the polarity-switching circuit. If some pins of the four-pin connector are jumped to each other, the device would still work, but the stimulation electrode will only be able to be driven lower than body ground—this is essentially a polarity-switching circuit bypass.

Screw-in mount for the stimulation electrode and body ground electrode plate, currently not used in the prototype.

Two-pin jumper breakout for development of the LTC3459's shutdown feature (not used).

Software Design

The heart of the device is a small 8-bit microcontroller from STMicroelectronics, STM8L15206T6. The software on this device was developed in ANSI C99 using IAR Embedded Workbench for STM8 (code-size-limited kick-start edition), in conjunction with ST's debugging tool for their STM8 and STM32 microcontrollers, called ST-LINK/V2. ST's standard peripheral code library for STM8L15x devices was used to create the source code specific to this MCU. An application code library for the M24LR04 NFC memory tag was used to communicate with it using I2C peripheral.

Software Requirements

The software requirements for this device were as follows:

The program must cyclically generate pulse timing, pulse magnitude, and pulse polarity signals to control the external hardware of the stimulator.

The program must respect the patient's need for inspiratory and expiratory phases of the breath cycle.

The output of the device must have programmable pulse length (PL), pulse frequency (PF), pulse magnitude (PM), inter-pulse resting period (IPR), stimulation-to-recharge scaling ratio (SRS), breathing rate (BR), and inspiratory time (IT). See FIG. 2 (in Section 4.3) for visual representation of these variables.

The device must update its stimulation settings on the very next breath after new settings are communicated to it via the NFC interface, to ensure proper responsiveness.

The device must remain in the lowest power states as much as possible to conserve the energy supplied to it by a battery unit.

Power Consumption Considerations

In implantable medical devices, the focus is always on power efficiency. The main consumers of energy in any embedded system are usually wireless modules and microprocessors. Using passive NFC communication instead of ZigBee, Bluetooth Low Energy, or any other short range wireless technologies eliminates the bulk of power consumption. On another front, however, a very power-conscious microcontroller was chosen. But even when using a power-optimized microprocessor, it is its software that ultimately determines the battery life.

In any microprocessor not furnished with an on-chip wireless module, the next main power consumer is its central processing unit (CPU). In low-power applications, the CPU on the device must be kept in low-power modes as much as possible, and tasks not explicitly requiring CPU activity must be accomplished using other on-chip hardware. This has been the main focus of software development of the DAPhNe stimulator.

Software Architecture

Figure 12:
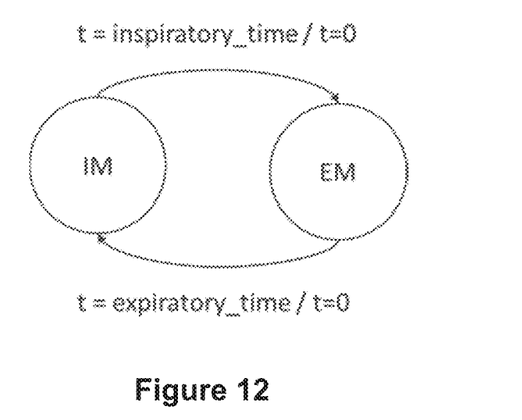
FIG. 12 is a diagram showing the two-state time-based state machine aspect of the DAPhNe stimulator.

The software architecture of the device is essentially a two-state time-based state machine (See FIG. 12). The device alternates between "inspiratory mode" (IM) and "expiratory mode" (EM); the transitions between these two states are triggered by the device's real-time clock (RTC) unit. While no biological feedback is shown, its use was contemplated. During IM, the device outputs stimulation and recharge pulses. During EM, the device updates its internal variables based on information read from its NFC memory and then rests until the next IM. CPU is kept inactive for as much time as possible, and RTC is used to wake up the CPU upon exiting the IM or EM.

Reducing CPU Duty Cycle

By "daisy-chaining" multiple on-chip hardware peripherals, stimulation control signals are achieved without active involvement of the CPU. Besides quickly checking the NFC memory for new data using I2C during EM and starting the peripheral event chain during IM, the CPU activity is not needed. During periods of computational inactivity, the device is put into one of two low-power modes.

Inspiratory Mode (IM): WFI Mode

At the beginning of IM, the CPU merely updates the RTC counter to an inspiratory time value (basically, sets a wake-up alarm for itself), and starts a hardware timer, TIM1. This timer triggers the chain of peripheral events explained further herein.

After updating RTC and TIM1, the CPU issues a Wait-For-Interrupt (WFI) instruction; in WFI mode, the CPU is stopped, while other peripherals are still running. As mentioned, the device "wake up" upon RTC overflow interrupt.

Expiratory Mode (EM): Active Halt Mode

Upon waking up from IM's WFI mode via an RTC interrupt, the device enters EM. Again, it updates the RTC counter value—this time, to count expiratory time. It disables TIM1 and TIM2 outputs, effectively shutting down the stimulation circuit, checks the NFC memory for new data using I2C protocol, and issues a "Halt" instruction. Because RTC has been enabled prior to the instruction, the device enters Active Halt mode. In this mode, CPU and all other peripherals except for RTC are stopped. This greatly reduces the device's power consumption.

Peripheral Chaining

The firmware uses the following hardware peripherals to accomplish the above cyclic biphasic pulse generation without involvement of CPU:

TIM1—advanced 16-bit control timer, used to control pulse timing (VTIM).

TIM2—general purpose 16-bit timer, used to control pulse polarity (VPOL)

TIM4—basic 8-bit timer, used to trigger digital-to-analog conversions.

DAC—12-bit digital-to-analog converter (DAC), used to control pulse magnitude (VMAG).

DMA—4-channel Direct Memory Access (DMA) controller, used to update peripheral memory registers.

Peripheral Event Flow

Figure 13:
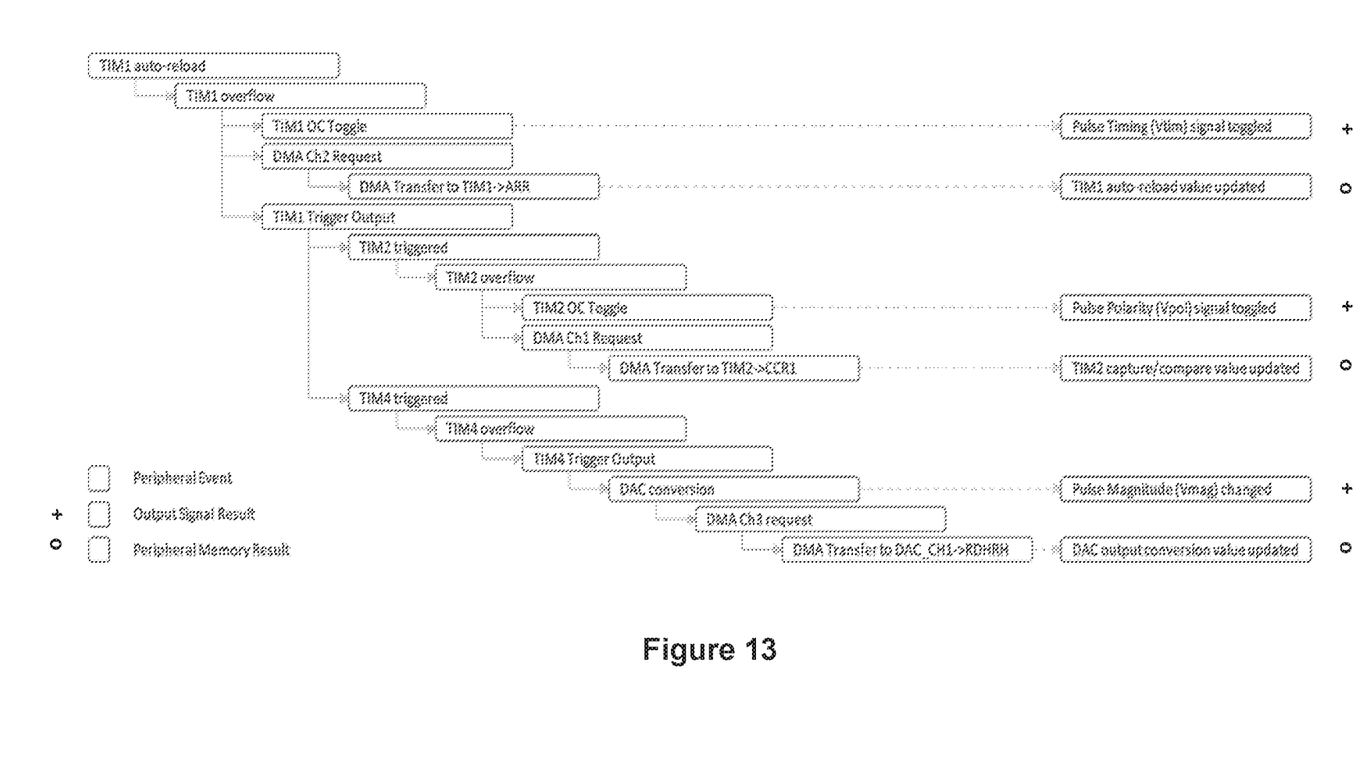
FIG. 13 is a diagram showing the hardware peripheral even chain that produces biphasic pulses.

FIG. 13 shows how the hardware peripherals are chained together to produce the biphasic pulses. This chain of events happens during each of the four pulse phases shown in FIG. 2c. The following sections explain FIG. 13 in greater detail.

TIM1

A new phase starts when TIM1 reaches its auto-reload value. During reload, it resets its counter to 0. The capture compare register of TIM1 is set to 0 permanently, so TIM1 actually overflows on the very next clock cycle. After that, it simply counts up to the auto-reload value.

Upon overflow, TIM1 issues an update event trigger flag. TIM1 toggles its pin output (effectively switching the current magnitude output signal on and off via an external MOSFET). It also issues an update event trigger flag polled by TIM2 and TIM4, and a transfer request on its DMA channel.

Upon request, DMA transfers a value from the device's random-access memory (RAM) into the TIM1_ARR (auto-reload) register. In effect, this controls when TIM1 overflows (and the rest of the chain starts over) next. A simple four value buffer, i.e. {150, 450, 1500, (1/PF—(150+100+1500)} (this example is in units of μs), supplied to the TIM1_ARR register would result in the stimulation circuit being on for 150 μs (stimulation phase), off for 450 μs (inter-pulse phase), on for 1500 μs (recharge phase), and off for the rest of the pulse period. The equivalent signal output from the TIM1 output pin can be seen in FIG. 3.

Upon being triggered on TIM1 overflow, TIM2 and TIM4 start counting up. They are configured as slaves to TIM1, and are being synchronized with it using update event triggers.

TIM2

On overflow or update event trigger from TIM1, TIM2 issues its own DMA request and toggles its own pin output, switching the polarity of the stimulation signal.

The same way that DMA controller updates the auto-reload register of TIM1, DMA also controls TIM2 timing. In this case, however, DMA transfers a RAM value into TIM2's capture compare register instead. When TIM2's counter reaches the capture/compare (CC) value, an overflow event is generated, and a DMA transfer request is issued. It is important to note, that TIM1 and TIM2 are clocked at the same exact frequency.

In this application, polarity of the signal should be switched right after the negative stimulation pulse to positive, and right after the positive stimulation pulse to negative, as shown in FIG. 3c. The software accomplishes this by feeding the DMA TIM2 channel a buffer storing {0xFFFF, 50, 0xFFFF, 50}. When the CC value is larger than TIM1's auto-reload value (i.e. 0xFFFF), TIM2 does not have time to reach overflow, and does not toggles its output. However, the TIM1 trigger event still forces TIM2 to issue a DMA request, updating its CC register to a low value (i.e. 50 clock cycles for stability). The effect of the above is that stimulation polarity switches only during the two resting phases (inter-pulse and rest), and never during the actual pulses.

TIM4

On TIM1 update event, TIM4 also is triggered. Unlike TIM2, TIM4 does not control any output signals by itself; it is simply used as a gateway to trigger DAC conversions and DMA requests. TIM4 is the only trigger source for DMA in medium density STM8L devices.

Upon TIM1 trigger, TIM4 starts counting up. However, its CC register is set to 1, so TIM4 overflows very quickly. It is also configured in "One Pulse" mode, meaning that after overflowing (and issuing an update event), it does not continue counting.

On its quick overflow, TIM4 issues its own update event trigger, which is polled in hardware by DAC.

DAC

On TIM4 update event trigger, DAC performs a conversion of its data register to an analog voltage on its pin output. Upon conversion, DAC issues a DMA transfer request on its configured DMA channel. DMA then transfers a value from RAM to the DAC data register, which is used on the next conversion (on the next phase). By feeding in a buffer like {(high value), (low value), (low value), (high value)}, DAC output assumes the waveform shown in FIG. 3d.

DMA

In short, the device uses three channels of the direct memory access controller to update the TIM1, TIM2, and DAC internal registers, and thus, alter the output signal of the stimulation circuit during each phase of the pulse cycle.

Peripheral Configuration Buffers

Three software buffers are used to pump data into the three peripheral registers using DMA. At run-time, these are stored in RAM after each NFC memory check and settings calculation. CPU starts TIM1 and shuts down; DMA starts cyclically loading these RAM buffers into TIM1's auto-reload register, TIM2's capture/compare register, and DAC's data register.

Figure 14:
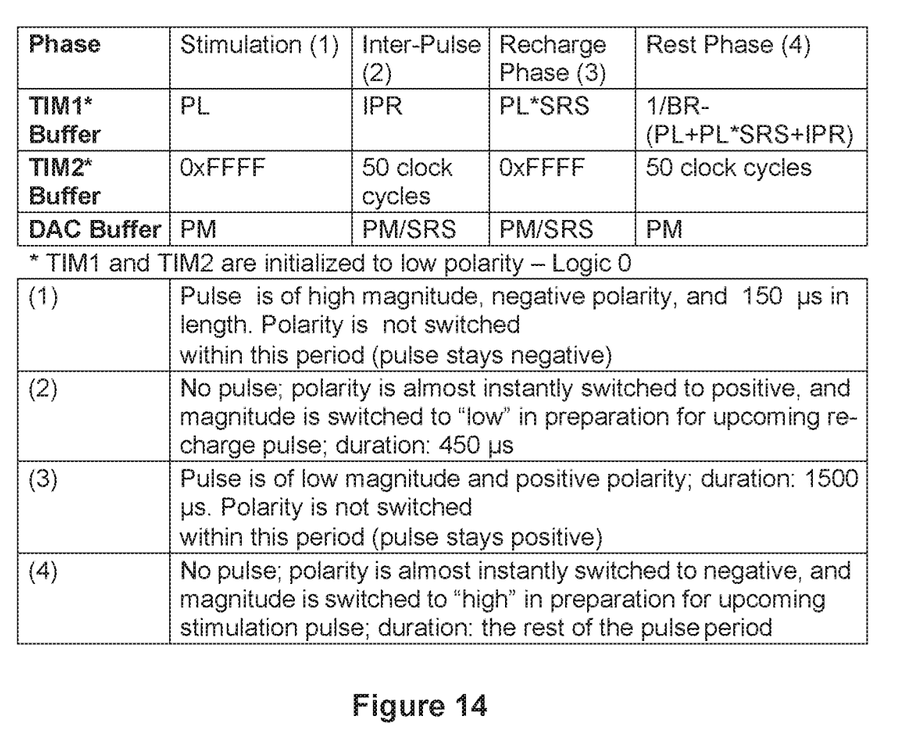
FIG. 14 is a table listing three four-value peripheral configuration buffers.

The table in FIG. 14 shows the three four-value buffers; first value is loaded prior to the stimulation phase, second—during inter-pulse phase, and so on. Effect of the shown values is explained below as well.

Safety Ending IM

At the end of IM, depending on the programmed inspiratory time, the pulse phase may be one of the four described above, although optimally, the device should arrive into the "resting" phase (Phase 4) for the duration of EM. When IM ends, the microcontroller starts the RTC counting up do expiratory time and polls the TIM1_ARR register. At each phase switch, it compares TIM1_ARR with the software buffer value for Phase 4 timing. If comparison result is false, it keeps going through the pulse phases until Phase 4 is achieved. At this point, the device continues with EM. This ensures that the last stimulation pulse cycle ends safely in Phase 4 before the device goes into EM.

NFC Data Exchange

At this prototype stage, no specific data protocol has been developed. An external device simply transmits a string of characters containing 5 comma-separated four-digit numbers.

The string is of type {0150, 0300, 2000, 1200, 0500}, meaning "150 µs PL, 3.00 mA PM, 20.00 bpm BR, 1.200 s IT, 500 µs IPR". PF is hardcoded to 20 Hz and SRS is hardcoded to 10, although both can easily be manipulated in the same way as PL, PM, BR, IT, and IPR with minor changes in code.

No backward communication protocol has been designed—reading from the NFC memory tag with an external transceiver simply returns the last communicated values.

As an external transceiver, the prototype uses a receiver board from the M24LR-DISCOVERY kit from ST Microelectronics, which contains the CR95HF-VMD5T transceiver chip. The kit comes with proprietary demo GUI software, which allows for easy data input.

It will be appreciated that the disclosed digitally adjustable phrenic nerve stimulator system provides novel and highly advantageous devices and methods used in providing stimulation pulses to the phrenic nerve to cause a diaphragm contraction and thereby provide a breath. The system provides an opportunity for controlling a patient's breathing, without being tethered to external devices. While the disclosed system is susceptible of embodiment in many different forms, the present disclosure can be considered as an exemplification of the principals of the invention and is not intended to limit the invention to the examples illustrated, and is only limited by the appended claims and legal equivalents thereof.

The invention claimed is:

1. A system for electrical ventilation stimulation of a patient, comprising:
   an implantable nerve stimulator including:
      a battery,
      a wireless power receiver electrically coupled to the battery,
      a central processing unit,
      a plurality of hardware peripherals including a first timer, a second timer, a third timer, a digital-to-analog converter, and a direct memory access controller;
      a near field communication memory tag including an adjustable setting, and
      a stimulation circuit electrically coupled to the battery, wherein an output of the stimulation circuit is controlled based on the adjustable setting by the central processing unit and the plurality of hardware peripherals;
      wherein the output of the stimulation circuit is biphasic charge-balanced pulses to stimulate a phrenic nerve, wherein the biphasic charge-balanced pulses comprise a negative stimulation pulse and a positive recharge pulse separated by an inter-pulse resting period (IPR), and wherein a pulse magnitude of the positive recharge pulse is smaller than that of the negative stimulation pulse by a stimulation-to-recharge scaling (SRS) ratio, and a pulse length of the positive recharge pulse is longer than that of the negative stimulation pulse by the SRS ratio; and
   an external digital programming device having near field communication transmission and a digital interface;
      wherein the external digital programming device is configured to change the adjustable setting of the implantable nerve stimulator.

2. The system of claim 1, wherein the implantable nerve stimulator utilizes an electrode for phrenic nerve stimulation and a subcutaneous anode plate.

3. The system of claim 1, wherein the external digital programming device utilizes wireless communication to change the adjustable setting of the implantable nerve stimulator.

4. The system of claim 3, wherein the wireless communication occurs via a near field communications network between the external digital programming device and the memory near field communication tag.

5. The system of claim 1, wherein the system automatically adjusts to bio-feedback mechanisms to operate the implantable nerve stimulator autonomously.

6. The system of claim 1, wherein the first timer is used to control pulse timing, the second timer is used to control pulse polarity, the third timer is used to trigger digital-to-analog conversions, the digital-to-analog converter is used to control pulse magnitude, and the direct memory access controller is used to update peripheral memory registers.

7. The system of claim 6, wherein the SRS=10.

* * * * *